US00PP33331P3

(12) United States Plant Patent
Nakanishi et al.

(10) Patent No.: US PP33,331 P3
(45) Date of Patent: Aug. 10, 2021

(54) ***FRAGARIA* L. PLANT NAMED 'TOCHIGI IW1 GO'**

(50) Latin Name: ***Fragaria* L. sp.**
Varietal Denomination: Tochigi iW1 Go

(71) Applicant: TOCHIGI PREFECTURE, Utsunomiya (JP)

(72) Inventors: Tatsuro Nakanishi, Utsunomiya (JP); Risa Tsurumi, Utsunomiya (JP); Takashi Ohashi, Utsunomiya (JP); Yoshiyuki Ishihara, Utsunomiya (JP)

(73) Assignee: TOCHIGI PREFECTURE, Utsunomiya (JP)

( * ) Notice: Subject to any disclaimer, the term of this patent is extended or adjusted under 35 U.S.C. 154(b) by 0 days.

(21) Appl. No.: 16/501,393

(22) Filed: Apr. 5, 2019

(65) Prior Publication Data

US 2020/0323116 P1 Oct. 8, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208, 209
See application file for complete search history.

(56) References Cited

U.S. PATENT DOCUMENTS

PP24,332 P2 * 3/2014 de Jongh ..... A01H 6/7409 Plt./208
PP31,082 P3 * 11/2019 de Jongh ..... A01H 6/7409 Plt./208
PP31,148 P2 * 12/2019 Nelson ..... A01H 6/7409 Plt./208

OTHER PUBLICATIONS

Tochigi Prefecture website. (http://www.pref.tochigi.lg.jp.e.sn.hp.transer.com/g04/ichigoiw1.html). Oct. 29, 2019. (Year: 2019).*
Tochigi Prefecture website-photo. (http://www.pref.tochigi.lg.jp.e.sn.hp.transer.com/g04/ichigoiw1.html). Oct. 29, 2019. (Year: 2019).*

* cited by examiner

*Primary Examiner* — Susan McCormick Ewoldt
*Assistant Examiner* — Karen M Redden

(57) ABSTRACT

'Tochigi iW1 Go' is a new variety of strawberry bred by crossbreeding variety 'Wadahatsukoi' and '09-52-1' in 2012. The plant may be used, e.g., for cultivation of fruit for consumption. 'Tochigi iW1 Go' is a high-quality, high-yielding variety that produces a fruit having a white pericarp, a large fruit size, a high-yielding characteristic, and adaptability to forcing culture.

8 Drawing Sheets

Plant name and variety denomination:

Latin name of the genus and species of the plant claimed: *Fragaria* L. sp.

Variety denomination: 'Tochigi iW1 Go'.

BACKGROUND

*Fragaria* is a genus of flowering plants in the Rosaceae family, commonly known as strawberries for their edible fruits. Strawberries have a taste that varies by cultivar, and ranges from quite sweet to rather tart. Strawberries are an important commercial fruit crop, widely grown in all temperate regions of the world.

Strawberries are cultivated worldwide for their fruit. The fruit is widely known for its characteristic aroma, bright red color, juicy texture, and sweetness. The strawberry is not, from a botanical point of view, a berry. Technically, it is an aggregate accessory fruit, meaning that the fleshy part is derived not from the plant's ovaries but from the receptacle that holds the ovaries.

Propagation is often by runners, which can be pegged down to encourage them to take root, or cut off and placed in a new location. Strawberries are popular plants to grow in the domestic environment, for consumption or exhibition purposes, almost anywhere in the world.

BRIEF SUMMARY

'Tochigi iW1 Go' is a new variety of *Fragaria* (*F.* x *ananassa*) bred by crossbreeding seedling series of variety 'Wadahatsukoi' (not patented) as the female parent and variety '09-52-1' (not patented) as the male parent in 2012. In 2013, a '13-w1-2' line was selected from among the crossbreeds and named 'Tochigi iW1 Go'. The plant may be used, e.g., for cultivation of fruit for consumption.

'Tochigi iW1 Go' is a high-quality, high-yielding variety that produces a fruit having a white pericarp, a taste and a quality similar to those of 'Tochiotome' (not patented), a large fruit size, a high-yielding characteristic, and adaptability to forcing culture. This line is a non-remontant strawberry for forcing culture, having been bred in development of varieties suitable for processing use, and has a characteristic that its fruit skin is pale-yellow.

'WADAHATSUKOI' (not patented) is a *Frageria* cultivar having medium to large fruit with a pinkish-white color.

'Tochigi iW1 Go' was asexually reproduced via runners in Tochigi-shi, Tochigi Japan.

DETAILED BOTANICAL DESCRIPTION OF THE PLANT

Figure 1:
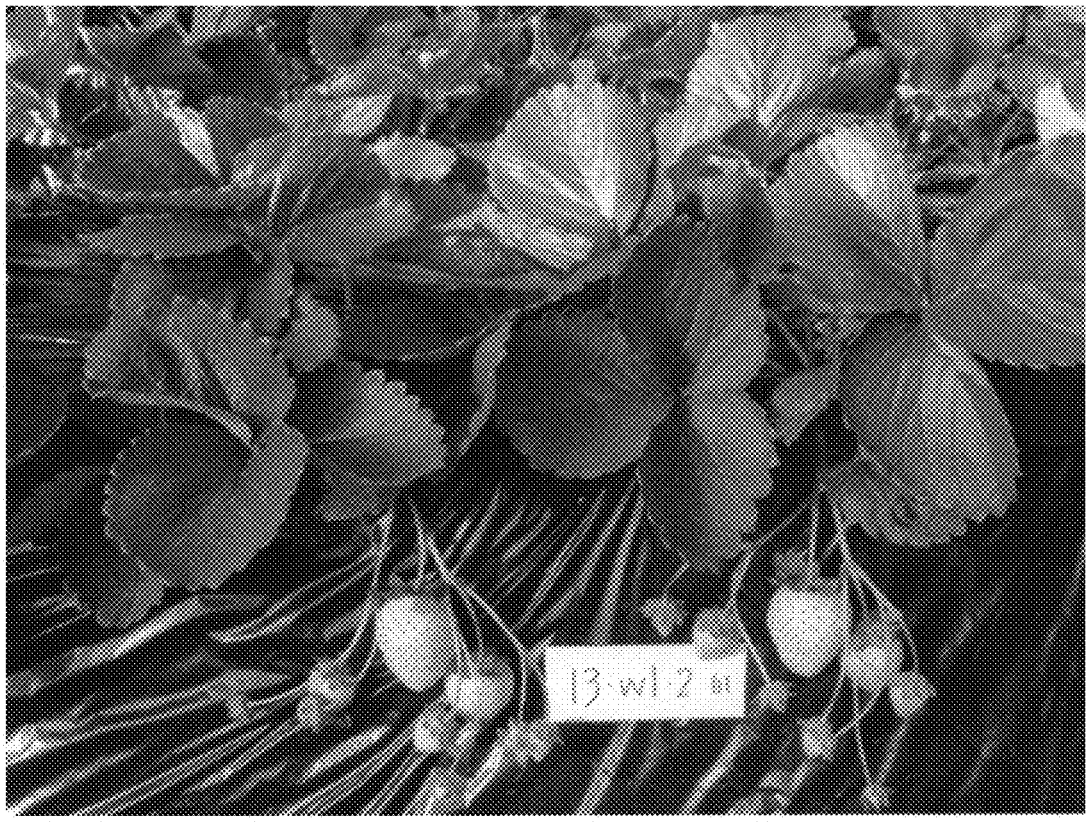
FIG. 1 is a photograph of a 'Tochigi iW1 Go' plant body at less than one year of age.

Variety: 'Tochigi iW1 Go'.

Species of the plant claimed: *Fragaris* L. The claimed plant is bred by crossbreeding seedling series of variety 'Wadahatsukoi' (not patented) as the female parent and variety '09-52-1' (not patented) as the male parent. The parental lines of the claimed plant resulted from the hybridization of different varieties. The parental lines of '09-52-1' are as follows: 'Tochigi 26 go' as the female parent and '98-7-3' as the male parent. The parental lines of 'Wadahatsukoi' are unknown.

Common names of the claimed plant's species include: Strawberry.

Characteristics of 'Tochigi iW1 Go' provided herein were observed when the plant was cultivated at Tochigi-shi, Tochigi, Japan in a simple vinyl greenhouse from 2012 to 2017. Descriptive terms used in Tables 1, 2, and 3 are consistent with the Japanese Examination Standard for *Fragaria* L., the entire contents of which are incorporated herein by reference. 'Tochigi iW1 Go' as described herein was crossbred around March and fixedly planted in September of the same year, and firstly selected around March three years later. The basic body at that time (basic line) was seven years old.

Properties and characteristics of 'Tochigi iW1 Go' are described in Table 1. Colors are described using The Royal Horticultural Society (R.H.S.) Colour Chart fourth edition.

TABLE 1

Properties and characteristics of 'Tochigi iW1 Go'

| Description | State of Expression |
|---|---|
| Plant: growth habit | spreading |
| Petal: color of upper side and lower side | RHS 155B (yellowish white) |
| Length of petals | 13.8 mm (second flower) |
| Width of petals | 15.0 mm (second flower) |
| Texture of petals | smooth |
| Fruit: size | large to very large; avg. weight per fruit 20 grams, width 46.3 mm (second fruits), length 57.8 mm (second fruits). |
| Fruit: shape | conical |
| Fruit (fruit skin): color | RHS 158C (pale-yellow) |

TABLE 1-continued

Properties and characteristics of 'Tochigi iW1 Go'

| Description | State of Expression |
|---|---|
| Fruit: color of flesh (excluding core) | RHS 155B (yellowish white) |
| Type of bearing | not remontant (one-season bearing) |

When grown in Tochigi-shi, Tochigi, Japan (or in an area with a similar latitude and climate) 'Tochigi iW1 Go' should be planted in mid-September. In this region, flowering time is from late October to early February. In this region, harvesting time is from early December to late March. The claimed variety 'Tochigi iW1 Go' can be stored for six days at a temperature of 5 degrees Celsius or lower.

Characteristic pretests were performed in 2015 and 2016 using 10 stocks per sector and a 2 sector system. Research items were growth, yield, and fruit quality. The test farm field used was a pipe house. Planting pattern used was soil culture, two high ridges with ridge width of 100 cm and distance between stocks of 24 cm. Start of heat retention was at the end of October. Temperature control was performed according to the following pattern: a morning temperature of 25° C., afternoon temperature of 23° C., and lowest night temperature of 8° C. from the end of October to mid-December; followed by a morning temperature of 27° C., afternoon temperature of 23° C., and lowest night temperature of 8° C. until late February; and finally a morning temperature of 25° C., afternoon temperature of 23° C., lowest night temperature of 8° C. after late February.

In 2015, forcing culture and cell nursing were used as cropping type and nursing method, and time of fix planting was late September. Base fertilizer content was 1.0 kg/a nitrogen, 1.2 kg/a phosphoric acid, and 0.8 kg/a potash. Additional fertilizer was used, with a content per one fertilization of 0.1 kg/a nitrogen, 0.04 kg/a phosphoric acid, and 0.06 kg/a potash. Additional fertilization was made basically every 14 days from late December until the end of culture.

In 2016, forcing culture, cell nursing, and night cooling nursing were used as cropping type and nursing method, and time of fix planting was early September for night cooling nursing and late September for cell nursing. Base fertilizer content was 2.0 kg/a nitrogen, 2.4 kg/a phosphoric acid, and 1.6 kg/a potash. No additional fertilizer was used.

The growth habit of 'Tochigi iW1 Go' is spreading, with a plant height of approximately 20 cm. Plant width has not yet been obtained. The leaf shape of 'Tochigi iW1 Go' is odd pinnate, with a dentate margin and reticulate venation pattern. The vein color of 'Tochigi iW1 Go' is RHS 139D (light yellow green). Leaf shape is circular and length is equal in relation to width. Leaf length is 20-23 cm in November and 17-20 cm in January. Leaf width is 9.3 mm in November. Blistering on the surface of the leaf is medium, and glossiness is medium. Leaf blade length of 'Tochigi iW1 Go' is 10-11 mm in November and 7-10 mm in January. Leaf width is 9-10 mm in November and approximately 6 mm in January (based on 2017 Research Report). Leaf color is green RHS 137B (grayish olive green) on the upper leaf surface and RHS 138B (grayish yellow green) on the lower leaf surface. Sepal color of 'Tochigi iW1 Go' is RHS 137A (grayish olive green), with a smooth texture. Leaflet shape is oval, and leaflet texture is smooth. Leaflet length is 10.1 cm in November, and leaflet width is 9.3 cm in November.

Leaflet color is RHS 137D (moderate yellow green) on upper surface and 137A (grayish olive green) on lower surface. Bud size is 8.9 mm (second flower) and bud color is RHS 139C (moderate yellow green). Bud shape is global. Average sepal length and width measurements have not been obtained. Petal length and width, and pedicle and peduncle length, of 'Tochigi iW1 Go' differ depending on inflorescence and time. Pedicle length is 8.8 cm (first fruits). Pedicle and peduncle color is RHS 139D (light yellow green). Peduncle length (length between base of peduncle and the point where branching starts) is 5.0 mm. Petal texture is smooth, margin is smooth, and color is RHS 155B (yellowish white). Average number of flowers per panicle for 'Tochigi iW1 Go' is 11-12. Flower diameter is 32.8 mm (second flower). Ovary color is RHS 154A (brilliant yellow green) with a conical shape, while anther color is RHS13A (vivid yellow) with a long heart shape. Measurements of ovary and anther size have not been obtained.

Figure 2:
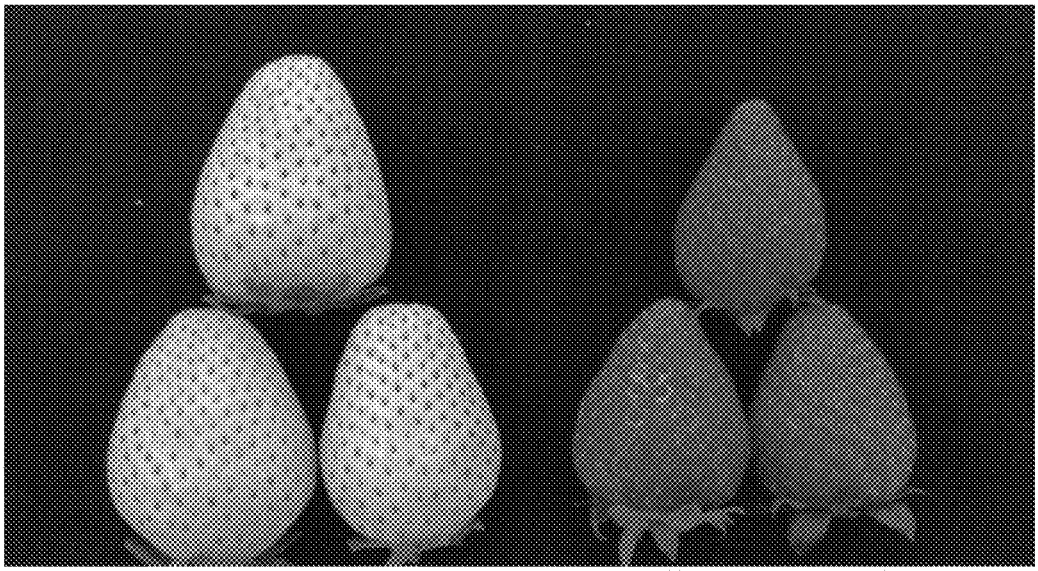
FIG. 2 is a photograph of the fruit of a 'Tochigi iW1 Go' plant (left) and the fruit of a 'Tochiotome' plant (right) at less than one year of age.
Figure 3:
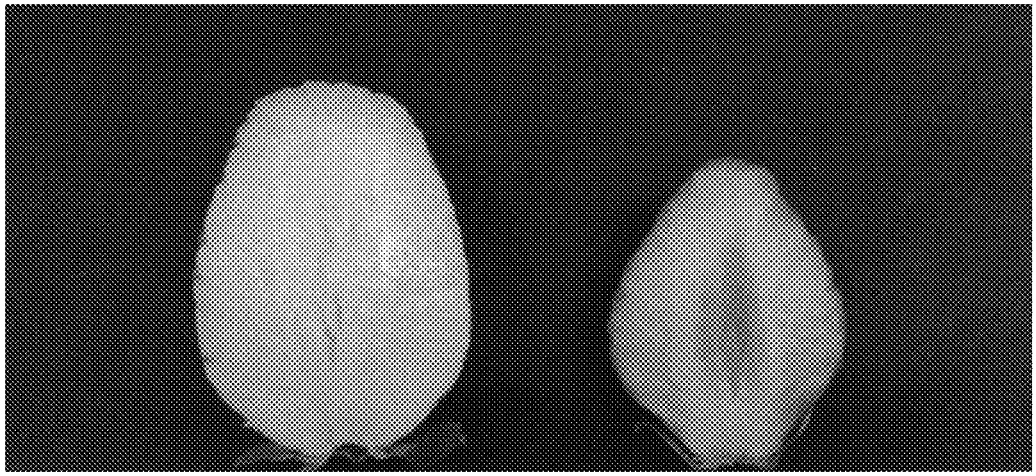
FIG. 3 is a photograph of a cross-sectional view of the fruit of a 'Tochigi iW1 Go' plant (left) and a cross-sectional view of the fruit of a 'Tochiotome' plant (right) at less than one year of age.

A variety that is similar to 'Tochigi iW1 Go' is 'Tochiotome'. Characteristics of 'Tochigi iW1 Go' and 'Tochiotome' are compared in Table 2. Fruit of 'Tochiotome' are shown in FIGS. 2 and 3.

TABLE 2

Distinguishable characteristics between 'Tochigi iW1 Go'and 'Tochitome'

| Denomination of Similar Variety | Description of Characteristics | State of Expression in Similar Variety | State of Expression in 'Tochigi iW1 Go' |
|---|---|---|---|
| TOCHIOTOME | Plant: growth habit | semi-upright | spreading |
| TOCHIOTOME | Fruit: size | Large, width 36.7 mm (second fruits), length 44.8 mm (second fruits) | large to very large, avg. weight per fruit 20 g, width 46.3 mm (second fruits), length 57.8 mm (second fruits) |
| TOCHIOTOME | Fruit (fruit skin): color | RHS 42A vivid red | RHS 158C pale yellow |
| TOCHIOTOME | Fruit: color of flesh (excluding core) | RHS 31C grayish reddish orange | RHS 155B yellowish white |
| TOCHIOTOME | Fruit: color of core | RHS 40C strong reddish orange | RHS 155B yellowish white |

Growth habit of 'Tochigi iW1 Go' is spreading. Vigor is similar to that of 'Tochiotome', and gets a bit weaker in a severely cold period. 'Tochigi iW1 Go' leaflet is a bit larger and roundish, and is colored green which is a bit paler than that of 'Tochiotome'. 'Tochigi iW1 Go' petiole length is similar to that of 'Tochiotome'. 'Tochigi iW1 Go' flower cluster is a straight-branch type, footstalk length is similar to that of 'Tochiotome', and the number of bearing of flowers at primary flower cluster is small.

Growth habit of 'Tochigi iW1 Go' is spreading. Lamina length, leaf width, and petiole length of 'Tochigi iW1 Go' are each similar to those of 'Tochiotome', and vigor is similar to that of 'Tochiotome', too. Flowering bud differentiation period is similar to or a bit earlier than that of 'Tochiotome', and time of beginning of flowering and time of beginning of harvesting are similar to or a bit later than those of 'Tochiotome'. The number of bearing of flowers at primary flower cluster is smaller than that of 'Tochiotome'.

The number of production of runners by 'Tochigi iW1 Go' is a bit smaller than that of 'Tochiotome', and rooting is slow. Flowering bud differentiation period comes a bit earlier than that of 'Tochiotome'. Response to a treatment for promoting flowering bud differentiation by low temperature and short-day is similar to that of 'Tochiotome', and differentiation is accelerated. Time of beginning of flowering and time of beginning of harvesting are similar to or a bit slower than those of 'Tochiotome'. No resistance to diseases and pests has been found so far. The number of days required for fruit to ripen from flowering to harvesting is similar to that of 'Tochiotome'.

Glossiness of 'Tochigi iW1 Go' fruit skin is as excellent as that of 'Tochiotome'. 'Tochigi iW1 Go' seeds are moderately below surface and are colored RHS 42A vivid red. Time suitable for harvesting can be determined based on the degree of coloring of seeds on a sun-lit surface. 'Tochigi iW1 Go' fruit pulp is colored RHS 155B (yellowish white), has a minute hollow, and does not have a characteristic fragrance. 'Tochigi iW1 Go' fruit shape is conical at primary flower cluster and primary axillary flower cluster, and is conical to long conical at secondary axillary flower cluster and subsequent flower clusters. Most of malformed fruits have a cylindrical shape and an ovoid shape. In and after severely cold period, deformed fruits with disordered tips (non-fertilized fruit and blue-tipped fruit) are likely to appear. Sugar content is 9.5 to 10.3 degrees, which is similar to that of 'Tochiotome'. 'Tochigi iW1 Go' fruit acidity is 0.49 to 0.54%, which is lower than that of 'Tochiotome'. 'Tochigi iW1 Go' fruit sugar-acid ratio is 18.8 to 20.1, which is higher than that of 'Tochiotome'. These indicate good eating quality. Firmness of fruit is 48-60 gf/φ2 mm, which is similar to or a bit softer than that of 'Tochiotome'.

Average weight per 'Tochigi iW1 Go' fruit is approximately 20 g, which is larger by 20% than that of 'Tochiotome', and a ratio of appearance of fruits with 22 g/fruit or more is as high as nearly 30%. Total yield is larger by 20% than that of 'Tochiotome'. Fruit length:width ratio of 'Tochigi iW1 Go' is 1.2:1 (this value is an average taken from 10 fruits). The fruit of 'Tochigi iW1 Go' has little to no hollow center. Productivity density of the fruit is 81.5 g/100 mL, which is equal to approximately 63.3 pounds per bushel.

In the case of cell nursing, the yield of salable fruit by 'Tochigi iW1 Go' is higher by approximately 20% than that of 'Tochiotome'. In the case of night cooling nursing, the yield of salable fruit is equal to or higher than that of 'Tochiotome'. In either of the tests and in either of the nursing methods, the weight per fruit is as large as approximately 20 g or more. As for the yield per flower cluster, the yield of the primary flower cluster and subsequent flower clusters is superior to that of 'Tochiotome'. As for the ratio of the number of fruit by class of fruit weight, the ratio of fruit having a weight of 22 g or more is higher than that of 'Tochiotome.'

Figure 4:
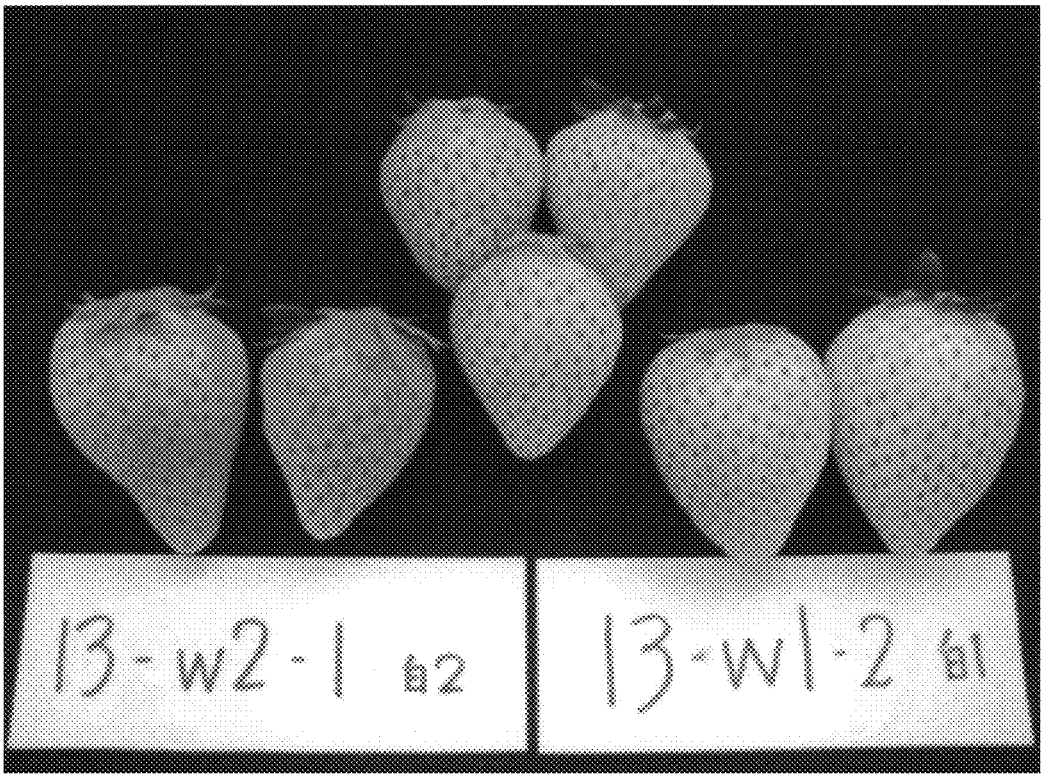
FIG. 4 is a photograph of the fruit of a 'Tochigi Shiro 2 Go' plant (left), the fruit of a 'Wadahatsukoi' plant (center), and the fruit of a 'Tochigi iW1 Go' plant (right) at less than one year of age.
Figure 5:
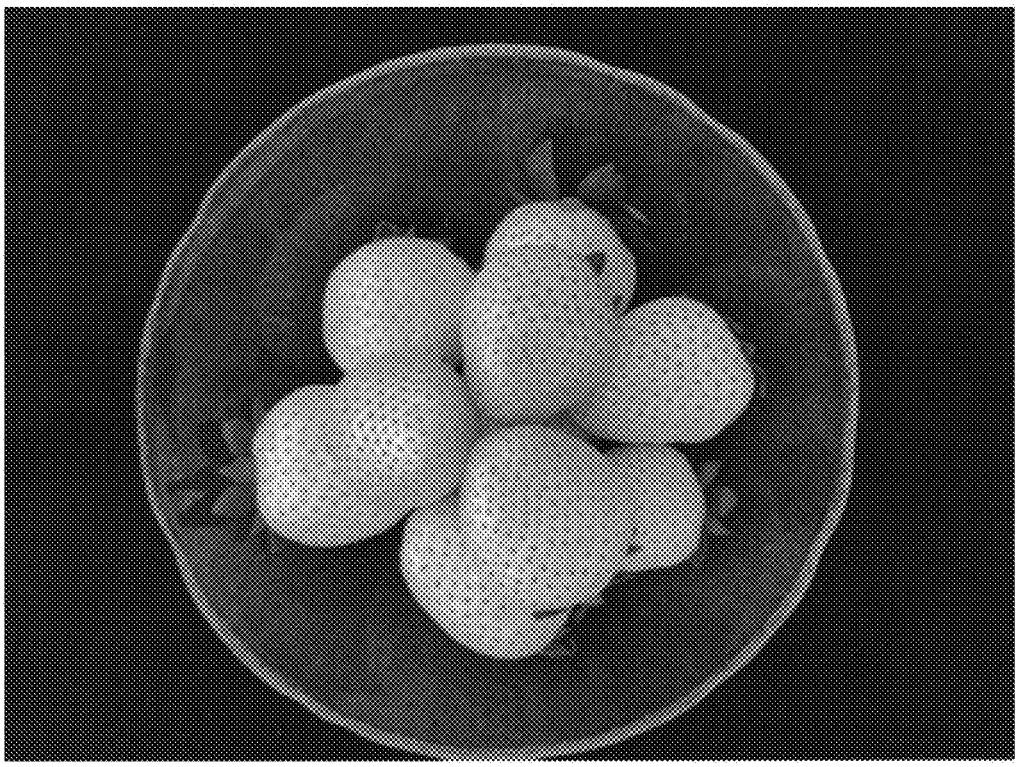
FIG. 5 is a photograph of the fruit of a 'Tochigi iW1 Go' plant at less than one year of age.
Figure 6:
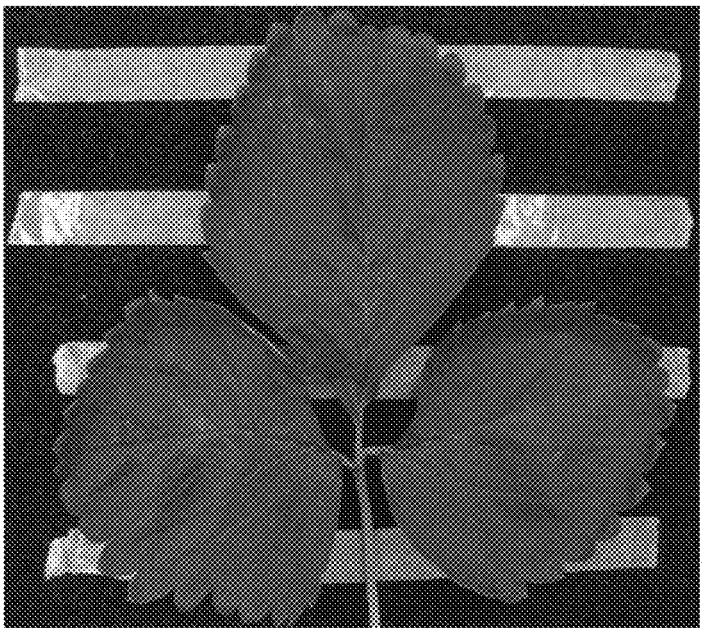
FIG. 6 is a photograph of the top surface of the leaf of a 'Tochigi iW1 Go' plant at less than one year of age.
Figure 7:
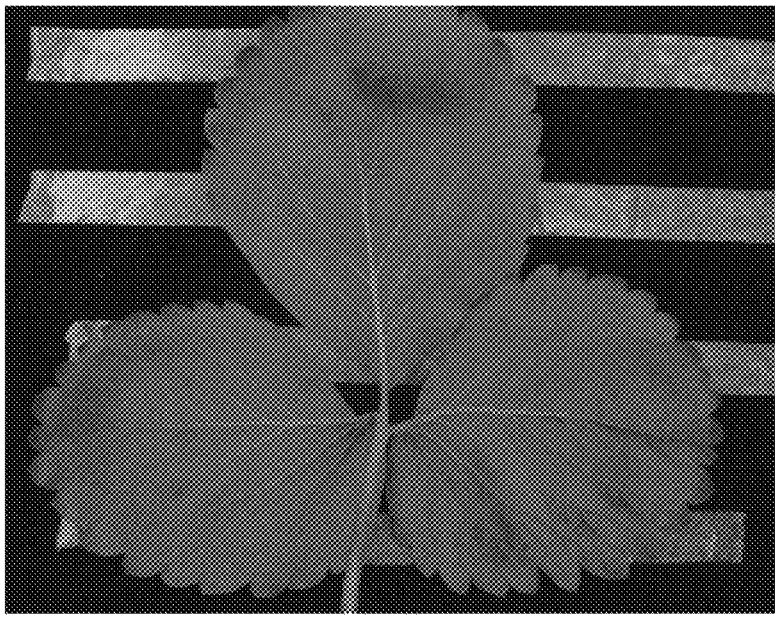
FIG. 7 is a photograph of the bottom surface of the leaf of a 'Tochigi iW1 Go' plant at less than one year of age.
Figure 8:
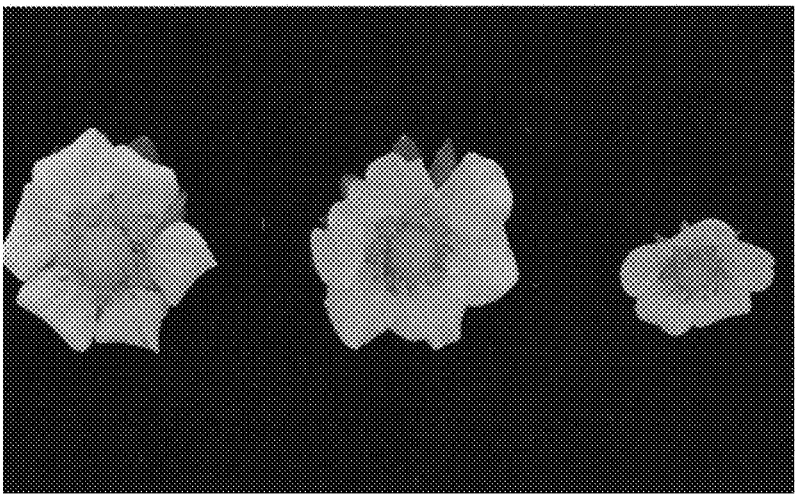
FIG. 8 is a photograph of the flowers of a 'Tochigi iW1 Go' plant at less than one year of age.

A comparison between 'Tochigi iW1 Go' and its parental varieties '09-52-1' and 'Wadahatsukoi' are provided in Table 3. Fruit of 'Wadahatsukoi' are shown in FIG. 4.

TABLE 3

Description of physical differences between parental plants

| Mother Variety | Description of Characteristics | State of Expression in Mother Variety | State of Expression in 'Tochigi iW1 Go' |
|---|---|---|---|
| WADAHATSUKOI | Fruit: size | Unknown | large to very large, avg. weight per fruit 20 g, width 46.3 mm (second |

TABLE 3-continued

| Description of physical differences between parental plants | | | |
|---|---|---|---|
| Mother Variety | Description of Characteristics | State of Expression in Mother Variety | State of Expression in 'Tochigi iW1 Go' |
| | | | fruits), length 57.8 mm (second fruits) |
| WADAHATSUKOI | Fruit (fruit skin): color | Unknown | RHS 158C pale yellow |
| 09-52-1 | Plant: growth habitat | Unknown | Spreading |
| 09-52-1 | Fruit: size | Unknown | Large to very large, avg. weight per fruit 20 g, width 46.3 mm (second fruits), length 57.8 mm (second fruits) |
| 09-52-1 | Fruit (fruit skin): color | RHS 32C strong yellowish pink | RHS 158C pale yellow |
| 09-52-1 | Fruit: color of flesh | 155A yellowish white | RHS 155B yellow white |
| 09-52-1 | Fruit: color of core | 40C strong reddish | yellowish white |

'Tochigi iW1 Go' fruit skin color is RHS 158C pale yellow, which is whiter than peach white color of 'Wadahatsukoi'. 'Tochigi iW1 Go' fruit shape is conical. The ratio of appearance of malformed fruits is similar to that of 'Tochiotome', and is larger than that of 'Wadahatsukoi'. Deformed fruits with disordered tips, such as non-fertilized fruit and blue-tipped fruit, are likely to appear. Although 'Tochigi iW1 Go' fruit sugar content is similar to or a bit lower than that of 'Tochiotome', acidity is lower and a sugar-acid ratio is higher, indicating generally good eating quality. Firmness of fruit is similar to that of 'Tochiotome' and is higher than that of 'Wadahatsukoi'.

It will be understood that the average size of the plant and fruit may vary with location, season, nutrition, irrigation, etc.

What is claimed is:

1. A new and distinct *Fragaria* L. plant named 'Tochigi iW1 Go' as illustrated and described.

* * * * *